US010865355B2

(12) United States Patent
Colozzi et al.

(10) Patent No.: US 10,865,355 B2
(45) Date of Patent: Dec. 15, 2020

(54) COS AND $CS_2$ ABATEMENT METHOD

(71) Applicant: STAMICARBON B.V., Sittard (NL)

(72) Inventors: Michele Colozzi, Rome (IT); Emma Palo, Rome (IT); Palma Contaldo, Rome (IT); Maria Rosaria Pepe, Rome (IT); Vincenzo Palma, Fisciano (IT); Vincenzo Vaiano, Fisciano (IT)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 15/677,984

(22) Filed: Aug. 15, 2017

(65) Prior Publication Data

US 2018/0023012 A1 Jan. 25, 2018

Related U.S. Application Data

(62) Division of application No. 14/773,263, filed as application No. PCT/NL2014/050157 on Mar. 14, 2014, now Pat. No. 9,765,272.

(30) Foreign Application Priority Data

Mar. 14, 2013 (EP) .................................... 13159258

(51) Int. Cl.
*C10L 3/10* (2006.01)
*B01D 53/14* (2006.01)
(Continued)

(52) U.S. Cl.
CPC .......... *C10L 3/103* (2013.01); *B01D 53/1456* (2013.01); *B01D 53/48* (2013.01);
(Continued)

(58) Field of Classification Search
None
See application file for complete search history.

(56) References Cited

U.S. PATENT DOCUMENTS 3,966,875 A 6/1976 Bratzler et al.
4,153,674 A 5/1979 Verloop et al.
(Continued)

FOREIGN PATENT DOCUMENTS

AU 2012216559 9/2012
CN 101080482 11/2007
(Continued)

OTHER PUBLICATIONS

Catalano et al. Packed Bed Reactors. Visual Encyclopedia of Chemical Engineering. pp. 1-6 http://encyclopedia.che.engin.umich.edu/Pages/Reactors/PBR/PBR.html (Year: 2011).*
(Continued)

*Primary Examiner* — Jelitza M Perez
(74) *Attorney, Agent, or Firm* — Morrison & Foerster LLP

(57) ABSTRACT

Disclosed is method for removing carbonyl sulphide and/or carbon disulphide from a sour gas stream. The method comprises subjecting the gas stream to simultaneous contact with an absorption liquid, such as an aqueous amine solution, and with a catalyst suitable for hydrolyzing carbonyl sulphide and/or carbon disulphide. To this end, the invention also provides a reactor system wherein both an absorption liquid and a catalyst are present. In a preferred embodiment, the catalyst is a heterogeneous catalyst present on or in an absorption column, either coated on the trays of a column with trays, or contained in the packing of a packed column.

10 Claims, 5 Drawing Sheets

(51) Int. Cl.

| | | |
|---|---|---|
| *B01D 53/48* | (2006.01) | |
| *B01J 23/06* | (2006.01) | |
| *B01J 23/22* | (2006.01) | |
| *B01J 23/26* | (2006.01) | |
| *B01J 23/28* | (2006.01) | |
| *B01J 23/34* | (2006.01) | |
| *B01J 23/46* | (2006.01) | |
| *B01J 23/745* | (2006.01) | |
| *B01J 23/755* | (2006.01) | |
| *B01J 19/24* | (2006.01) | |
| *C07C 7/148* | (2006.01) | |

(52) U.S. Cl.
CPC ............ *B01J 19/24* (2013.01); *B01J 23/06* (2013.01); *B01J 23/22* (2013.01); *B01J 23/26* (2013.01); *B01J 23/28* (2013.01); *B01J 23/34* (2013.01); *B01J 23/462* (2013.01); *B01J 23/745* (2013.01); *B01J 23/755* (2013.01); *C07C 7/14875* (2013.01); *B01D 2257/308* (2013.01); *B01J 2219/24* (2013.01); *C10L 2290/06* (2013.01); *C10L 2290/541* (2013.01)

(56) References Cited

U.S. PATENT DOCUMENTS

| | | | |
|---|---|---|---|
| 4,482,529 A | 11/1984 | Chen et al. | |
| 4,524,050 A | 6/1985 | Chen et al. | |
| 6,096,280 A * | 8/2000 | Ellenor | B01D 53/52 423/242.1 |
| 6,113,872 A | 9/2000 | Nougayrede | |
| 6,322,763 B1 | 11/2001 | McDaniel | |
| 2006/0131216 A1 | 6/2006 | Scheirer et al. | |
| 2006/0272502 A1* | 12/2006 | Van Grinsven et al. | B01D 53/1425 95/235 |
| 2009/0050533 A1* | 2/2009 | Ripperger | C10L 3/00 208/208 R |

FOREIGN PATENT DOCUMENTS

| | | |
|---|---|---|
| EP | 0214407 | 3/1987 |
| EP | 0997188 | 5/2000 |
| EP | 0 927 142 | 3/2001 |
| EP | 2248575 | 11/2010 |
| GB | 1 563 251 | 3/1980 |
| WO | WO-9614135 | 5/1996 |
| WO | WO-0035806 | 6/2000 |
| WO | WO-2008148077 | 12/2008 |
| WO | WO-2009117546 | 9/2009 |
| WO | WO-2009117550 | 9/2009 |
| WO | WO-2010060978 | 6/2010 |
| WO | WO-2010115898 | 10/2010 |
| WO | WO-2011033191 | 3/2011 |
| WO | WO-2012/107641 | 8/2012 |
| WO | WO-2013120166 | 8/2013 |

OTHER PUBLICATIONS

Eigenberger, G. Fixed-Bed Reactors. Industrial Reactors. vol. B4, pp. 199-238 https://elib.uni-stuttgart.de/bitstream/11682/1848/1/eig16.pdf (Year: 1992).*

Naik et al. Absorbers. Visual Encyclopedia of Chemical Engineering, Coolege of Engineering, Univeristy of Michigan. pp. 1-34 http://encyclopedia.che.engin.umich.edu/Pages/SeparationsChemical/Absorbers/Absorbers.html (Year: NA) (Year: NA).*

Catalano et al. Packed Bed Reactors. Visual Encyclopedia of Chemical Engineering, College of Engineering, University of Michigan . ppgs. http://encyclopedia.che.engin.umich.edu/Pages/Reactors/PBR/PBR.html (Year: NA) (Year: NA).*

Farlex-filled-definition. Thefreedictionary.com https://www.thefreedictionary.com/filled (Year: NA) (Year: NA).*

Eigenberger, G. Fixed Bed Reactors. Ullman's Encyclopedia of Industrial Chemistry. vol. B4. pp. 199-238 https://elib.uni-stuttgart.de/bitstream/11682/1848/1/eig16.pdf (Year: 1992).*

International Search Report and Written Opinion for PCT/NL2014/050157, dated Oct. 21, 2014, 26 pages.

Search Report directed to CN 201810442639.3, dated Apr. 23, 2020, 4 pages.

* cited by examiner

COS AND $CS_2$ ABATEMENT METHOD

CROSS-REFERENCE TO RELATED APPLICATIONS

This Application is a Division of application Ser. No. 14/773,263, having an international filing date of 14 Mar. 2014, now allowed, which is the national phase of PCT application PCT/NL2014/050157 having an international filing date of 14 Mar. 2014, which claims benefit of European patent application No. 13159258.6 filed 14 Mar. 2013. The contents of the above patent applications are incorporated by reference herein in their entirety.

FIELD OF THE INVENTION

The invention pertains to the removal of carbonyl sulphide (COS) and/or carbon disulphide ($CS_2$) from gas containing it, typically raw natural gas. Particularly, this regards the treatment of sour gas and/or natural gas.

BACKGROUND OF THE INVENTION

Natural gas typically consists of low hydrocarbons such as methane and some level of acidic impurities. Untreated natural gas is commonly referred to as sour gas. Before being able to use the natural gas, the acidic impurities need to be removed. This is commonly known as sweetening. Typical impurities are $CO_2$, $H_2S$, mercaptans (R—SH), carbonyl sulphide and/or carbon disulphide.

In the art, gases, other than untreated natural gas, comprising $H_2S$ and COS are sometimes also referred to as "sour gas." This concerns, in addition to natural gas, synthesis gas, gas produced by coal gasification, or fumes from a combustion process. In the present description, the term "sour gas" generally indicates a gas comprising $H_2S$ and COS, and requiring deacification, and more particularly indicates, preferably, untreated natural gas.

Known methods for removing acidic impurities employ absorption in amine solutions. However, this method is not suitable for the removal of carbonyl sulphide (O=C=S; mostly known as COS) and carbon disulphide (mostly known as $CS_2$). Regulatory changes require a further reduction of all sulfur containing compounds including COS.

A known method for removing COS and $CS_2$ consists of a two-step process, where in a first step, the COS and $CS_2$ is converted into $H_2S$. In a second reactor the $H_2S$ is removed. In another method, in a first reactor the COS and $CS_2$ are hydrolyzed and in a second reactor again the $H_2S$ is removed. A disadvantage of the latter method is that the absorption liquid does not efficiently absorb $H_2S$, COS and $CS_2$ at the same time. Particularly in the event that relatively high levels of $H_2S$ are present (which is typical for sour gas), the removal of COS and $CS_2$ can be insufficient.

A method that has been proposed to solve this bottleneck, involves the heterogenic, catalytic conversion of contaminants including COS and $CS_2$ into hydrogen sulphide in a separate hydrogenation reactor operating in the gas phase. As a catalyst, typically heavy metals such as iron, lead, molybdenum, nickel, tungsten or sulphide of these metals are employed. A disadvantage of this method is that high operating temperature is needed (200° C.-300° C.).

Therefore, it has been suggested in the alternative to treat gases at such high temperature with basic reacting salts of inorganic or organic bases or any mixtures of them, dissolved in water or alcohol, i.e. with a basic scrubbing medium, so that the contaminants COS and $CS_2$ are changed by means of hydrolysis into hydrogen sulphide according to the equilibrium reactions: (COS+$H_2O \leftrightarrow CO_2$+$H_2S$ and $CS_2$+2$H_2O \leftrightarrow CO_2$+2$H_2S$). The hydrogen sulphide can in turn be removed together with the host gas from the reaction zone. In that practice, the hydrolysis reaction is limited by the equilibrium constant. When the partial pressure of $H_2S$ reaches the equilibrium a relatively high level of COS and $CS_2$ remains in the emissions.

Further, another problem is incurred in the event that a basic absorbing liquid is used. For, the basicity of the absorbing medium has to be maintained in spite of the presence of $H_2S$ and $CO_2$. These compounds are to be converted into sulphides and carbonates thus reducing the basicity of the material as a whole. The hydrogen sulphide that is present as well as the hydrogen sulphide that is formed catalytically will then have to be removed from the gas in a separate step.

Some background art addresses the treatment of gas, other than natural gas, in order to deacidify such gases that contain H2S and COS, or at least remove COS therefrom. E.g., WO 00/35806 concerns the removal of COS from synthesis gas, in particular synthesis gas produced by gasification of coal. Such gas is essentially different from natural gas. In particular, the process in WO 00/35806 relates to the removal of COS from gasified coal or mixtures containing coal. In this gasification process the synthesis gas that is produced includes particulate matter such as coal ash, which is later used as the catalyst. The untreated natural gas does not contain this particulate matter as it consists typically of low hydrocarbons such as methane.

It is desired to improve the removal of COS and/or $CS_2$ from sour gas, preferably from natural gas, particularly untreated natural gas, and more particularly to provide a process that is capable of removing COS and/or $CS_2$ more efficiently, yet avoiding the high temperatures required in the art.

SUMMARY OF THE INVENTION

In order to better address one or more of the foregoing desires, the invention presents, in one aspect, a method for removing carbonyl sulphide and/or carbon disulphide from an untreated natural gas stream comprising subjecting the gas stream to contact with an absorption liquid so as to provide an absorbed gas-containing liquid, and bringing the absorbed gas-containing liquid in contact with a catalyst suitable for hydrolyzing carbonyl sulphide and/or carbon disulphide.

In a further aspect, the invention provides a method for removing carbonyl sulphide and/or carbon disulphide from a sour gas stream, comprising subjecting the gas stream to contact with an absorption liquid so as to provide an absorbed gas-containing liquid, and bringing the absorbed gas-containing liquid in contact with a catalyst suitable for hydrolyzing carbonyl sulphide and/or carbon disulphide, wherein the catalyst is a homogenous catalyst.

In another aspect, the invention pertains to a reactor system for removing carbonyl sulphide and/or carbon disulphide from a sour gas stream, the reactor system being filled with an absorption liquid and comprising a catalyst suitable for hydrolyzing carbonyl sulphide and carbon disulphide.

In a further aspect, the invention pertains to a sulfur recovery facility comprising the foregoing reactor system.

In a still further aspect, the invention pertains to a sulfur recovery facility comprising a. an acid gas removal unit comprising an absorber, operating at high pressure (HP), medium pressure (MP), or low pressure (LP), and an LP regenerator;
b. an acid gas enrichment/tail gas treatment unit comprising an LP/Low LP absorber and an LP regenerator;
c. a sulfur recovery unit;
d. a $COS/CS_2$ hydrolysis reactor;

wherein the $COS/CS_2$ hydrolysis reactor position is selected from (i) the top of the HP/MP/LP absorber; (ii) between the bottom of the HP/MP/LP absorber and the LP regenerator; and (iii) between the bottom of the LP/LLP absorber and the LP regenerator.

DETAILED DESCRIPTION OF THE INVENTION

Figure 1:
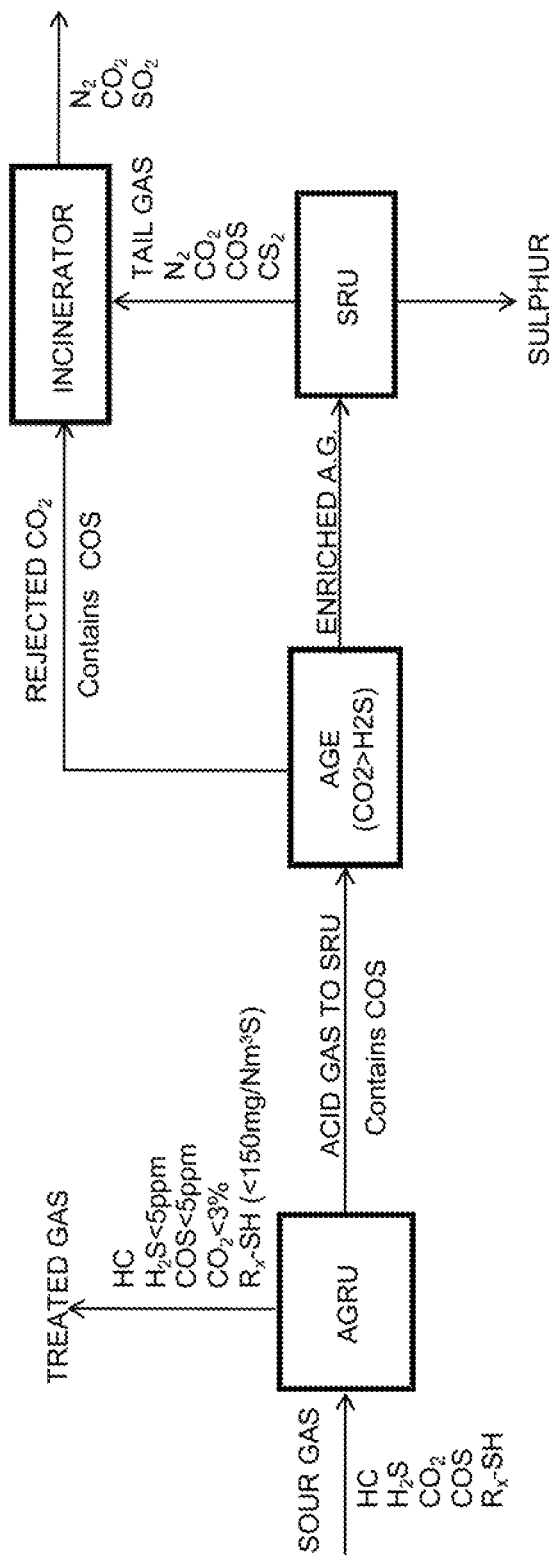
FIG. 1 is a schematic drawing of a conventional sulphur recovery facility.

In a broad sense, the invention is based on the judicious insight that the removal of $COS$ and/or $CS_2$ from a sour gas stream can be conducted more efficiently, and at a relatively low temperature, if one combines the actions of an absorption liquid and catalytic hydrolysis into one and the same medium.

To this end, the gas stream is subjected to contact with an absorption liquid so as to provide an absorbed gas-containing liquid, and the absorbed gas-containing liquid is contacted with a catalyst suitable for hydrolyzing carbonyl sulphide and/or carbon disulphide. It will be understood that the absorbed gas can refer to gas bubbles introduced in the absorption liquid (i.e. a two-phase system having the gas still in the gas phase), to molecularly absorbed compounds (i.e. the gas, components from the gas, or compounds converted from the gas such as $H_2S$ being in the liquid phase), or to a combination thereof.

In one embodiment, the foregoing is realized by subjecting the gas stream to simultaneous contact with the absorption liquid and with the catalyst. Particularly, the method of the invention is thereby conducted in a single reaction vessel. Without wishing to be bound by theory, the present inventors believe that the hydrolysis of $COS$ and/or $CS_2$ advantageously affects also the action of the absorption liquid, as it converts $COS$ and/or $CS_2$ into compounds that are more easily absorbed. It will be understood that this advantage will be particularly exhibited in the event that the absorbed gas-containing liquid contains the absorbed gas as bubbles (i.e. in the gas phase). For, in that case, the conversion will lead to compounds that are more easily molecularly retained in the absorption liquid, or even absorbed therein molecularly.

In this description, the impurities addressed (e.g. in respect of the removal, absorption, hydrolysis, and abatement) are described as carbonyl sulphide and/or carbon disulphide ($COS$ and/or $CS_2$). It will be understood that this refers to either or both of the compounds mentioned. I.e., it can be foreseen to address $COS$ only, $CS_2$ only, or $COS$ and $CS_2$. In other words, the impurities addressed are selected from the group consisting of carbonyl sulphide, carbon disulphide, and mixtures thereof.

The absorption liquid serves to absorb said impurities $COS$ and/or $CS_2$ from the gas stream treated. Liquids suitable for this purpose are known to skilled person. These can be based, e.g., on alcohol (methanol) or water. Absorption liquids can be physical solvents or solutions. A preferred absorption liquid is a basic aqueous solution, more preferably an amine solution. Suitable amines include MEA (mono ethanol amine), DEA (diethanol amine), MDEA (methyl diethanol amine), DIPA (diisopropyl amine), DGA (diglycol amine) or special formulated amine solution. Commercial physical solvents, or their mixtures, with or without additives can also be used. The absorption liquid can be a mixture of liquids.

The catalyst comprises a catalytically active metal, preferably a transition metal or a salt of a transition metal, more preferably selected from the group consisting of vanadium, iron, molybdenum, ruthenium, manganese, chromium, zinc, nickel, combination of them and salts thereof.

Thereby, typically if in the salt form, the catalyst can be a homogenous catalyst dissolved in the absorption liquid. In this embodiment, the invention is particularly useful in a method for removing carbonyl sulphide and/or carbon disulphide from a sour gas stream, i.e. a gas comprising $H_2S$ and $COS$ which is not necessarily an untreated natural gas.

More preferably, however, the catalyst is a heterogeneous catalyst, deposited on a suitable support. The latter is of advantage with a view to recovering and regenerating the catalyst particles. Suitable catalysts, and optionally supports, adjuvants and/or promoters, are generally known to the skilled person.

The present inventors do not particularly aim at providing a novel catalyst for $COS$ and/or $CS_2$ hydrolysis. Rather, based on the state of the art in $COS$ and/or $CS_2$ catalytic conversion, the invention particularly resides in the novel combination of such a catalytic step into a step of scrubbing with an absorption liquid. The invention also allows to optimize the process scheme configuration, as well as to profit from optimized operating parameters, mainly temperature and residence time.

In a particularly preferred embodiment, the catalyst is a heterogeneous catalyst presented on an absorption column as used in the absorption step. Thus, the catalyst can, e.g., be deposited on the trays of a column or on the packing of the same. It can be also deposited, in addition to the column or in lieu thereof, in special devices like filtering systems, special packing system outside the column, particularly downstream from where the gas stream is contacted with the absorption liquid.

Advantageously, in accordance with the invention the carbonyl sulphide and/or carbon disulphide are preferably hydrolyzed at a temperature below 150° C., preferably below 130° C.

In preferred embodiments, the reactor for $COS$ and/or $CS_2$ hydrolysis operates at low pressure (generally 0.01 to 0.1 barg, typically about 0.05 barg). This represents an advantage as compared to known COS and/or $CS_2$ removal, which typically occurs in a high-pressure absorption step. In fact, this adds to the residence time of the gas in the reactor, which contributes to further lowering the amount of COS in the gas stream. The simultaneous hydrolytic conversion of COS and/or $CS_2$ also helps to overcome the drawbacks associated with the fact that the basicity of the scrubbing liquid (i.e. the amine solution) inevitably becomes reduced during COS and/or $CS_2$ absorption.

The invention further pertains to a reactor system for removing carbonyl sulphide and/or carbon disulphide from a sour gas stream. The reactor system is filled with an absorption liquid (i.e., in particular an absorption liquid is made to pass through the system, preferably involving regeneration and recirculation of the regenerated liquid), and comprises a catalyst suitable for hydrolyzing carbonyl sulphide and carbon disulphide. In one embodiment, this reactor system comprises a single reaction vessel filled with the absorption liquid, said liquid also comprising the catalyst. In one preferred embodiment, the reactor is a column with trays, wherein the catalyst is a heterogeneous catalyst applied as a coating on the trays. In another preferred embodiment, the column is a packed column, wherein the catalyst is coated on the packing. Suitable packing materials are known to the skilled person and include, e.g., stainless steel or ceramic material, such as alumina.

It is also possible, in embodiments of the reactor system that the catalyst is deposited on one or more available contacting devices other than a column, such as a filtering media, plates designed to separate liquid from gas such as vane packs, corrugated plates, coalescing media, and flashing devices.

A particular advantage of the invention is represented by the flexibility in the location of the additional step for COS and/or $CS_2$ abatement. The first embodiment foresees the use of this reactor on the treated gas stream of an AGR unit (see FIG. 3), i.e. on the top of the absorber (which can be a HP, an MP, or an LP absorber, with HP being preferred. In this embodiment, after the COS and/or $CS_2$ hydrolysis reactor, a subsequent stage (not shown) is dedicated to the removal of the produced $H_2S$ and thereby reactivating the used absorption liquid, e.g. amine. Thus, in this embodiment, a two stage type of vessel can be employed, if desired a plurality thereof.

The abbreviations used for the various pressure sections referred to in this description have the following meanings:
LLP stands for very low pressure, typically 0.01-1 barg;
LP stands for low pressure, typically 1-20 barg;
MP stands for medium pressure, typically 20-40 barg;
HP stands for high pressure, typically greater than 40 barg.

In further preferred embodiments, the COS and/or $CS_2$ hydrolysis reactor is positioned either between the bottom of the HP/MP/LP absorber and the LP regenerator, or between the bottom of the LP/LLP absorber and the LP regenerator.

Thus, with reference to the foregoing embodiments, the invention pertains to a sulfur recovery facility comprising
a. an acid gas removal unit comprising an absorber, operating at high pressure (HP), medium pressure (MP), or low pressure (LP), and an LP regenerator;
b. an acid gas enrichment/tail gas treatment unit comprising an LP/LLP absorber and an LP regenerator;
c. a sulfur recovery unit;
d. a COS and/or $CS_2$ hydrolysis reactor;
wherein the COS and/or $CS_2$ hydrolysis reactor position is selected from (i) the top of the HP/MP/LP absorber; (ii) between the bottom of the HP/MP/LP absorber and the LP regenerator; and (iii) between the bottom of the LP/LLP absorber and the LP regenerator. The reactor mentioned under d. can be a customary-type hydrogenator/hydrolysis reactor, operating with the reagents in the gaseous phase, and wherein the catalyst preferably is a CoMox based catalyst (cobalt molybedenum oxide catalyst).

DETAILED DESCRIPTION OF THE FIGURES

FIG. 1 is a schematic drawing of a conventional sulphur recovery facility. Depicted is (a) a feed stream of sour gas entering into an Acid Gas Removal Unit (AGRU); (b) a stream of treated gas exiting the AGRU; (c) a stream of acid, COS-containing gas fed to a sulphur recovery unit (SRU) via an Acid Gas Enrichment unit (AGE); (d) a resulting stream of enriched acid gas fed to the SRU and rejected $CO_2$ fed to an incinerator; (e) a stream of tail gas from the SRU fed to the incinerator; (f) a stream of recovered sulphur from the SRU.

Figure 2:
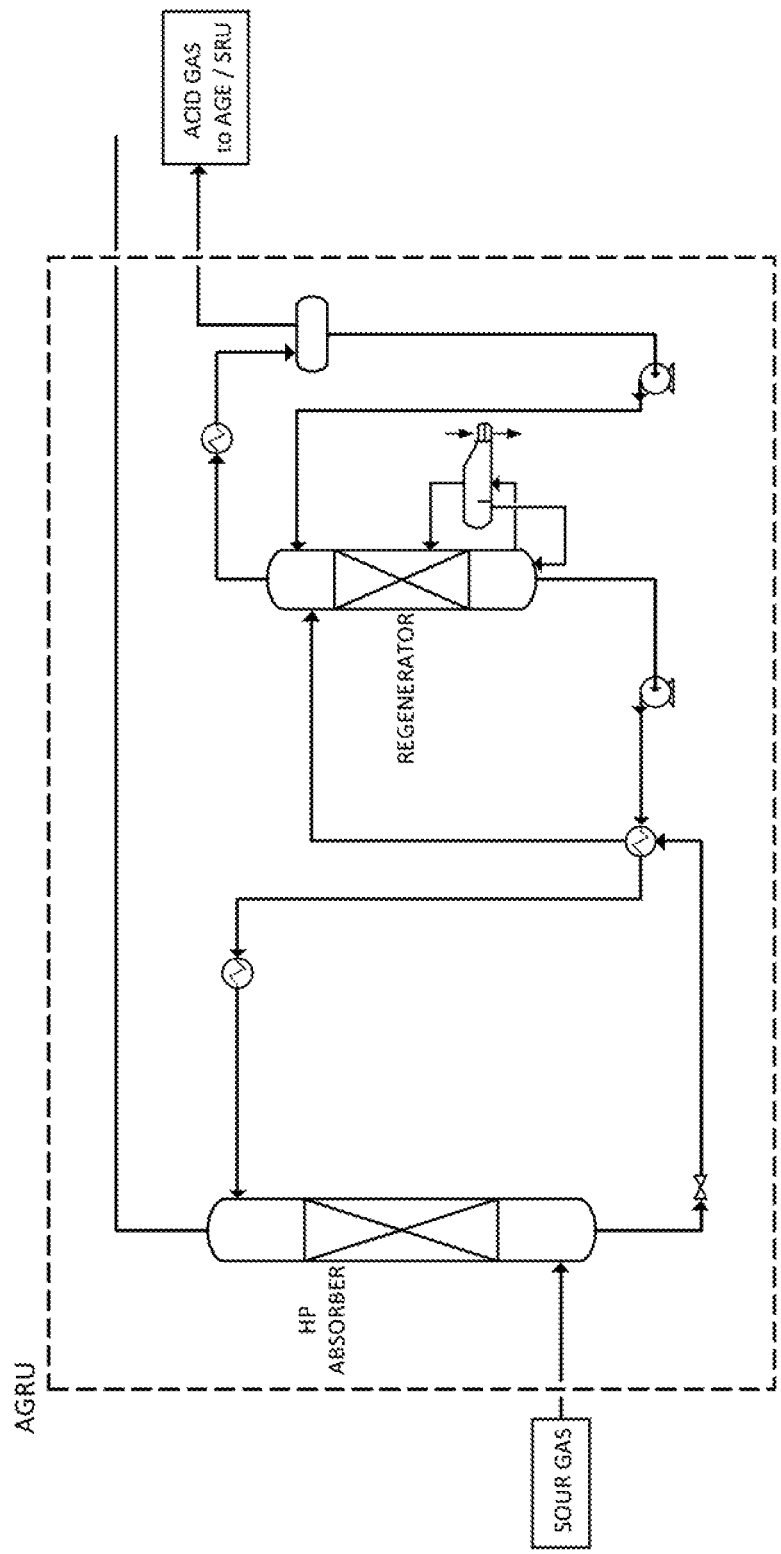
FIG. 2 is a schematic drawing of an acid gas removal unit of a conventional sulphur recovery facility.

FIG. 2 is a schematic drawing of the acid gas removal unit (AGRU) of the above conventional sulphur recovery facility. Shown is how an HP absorber and a regenerator are connected.

Figure 3:
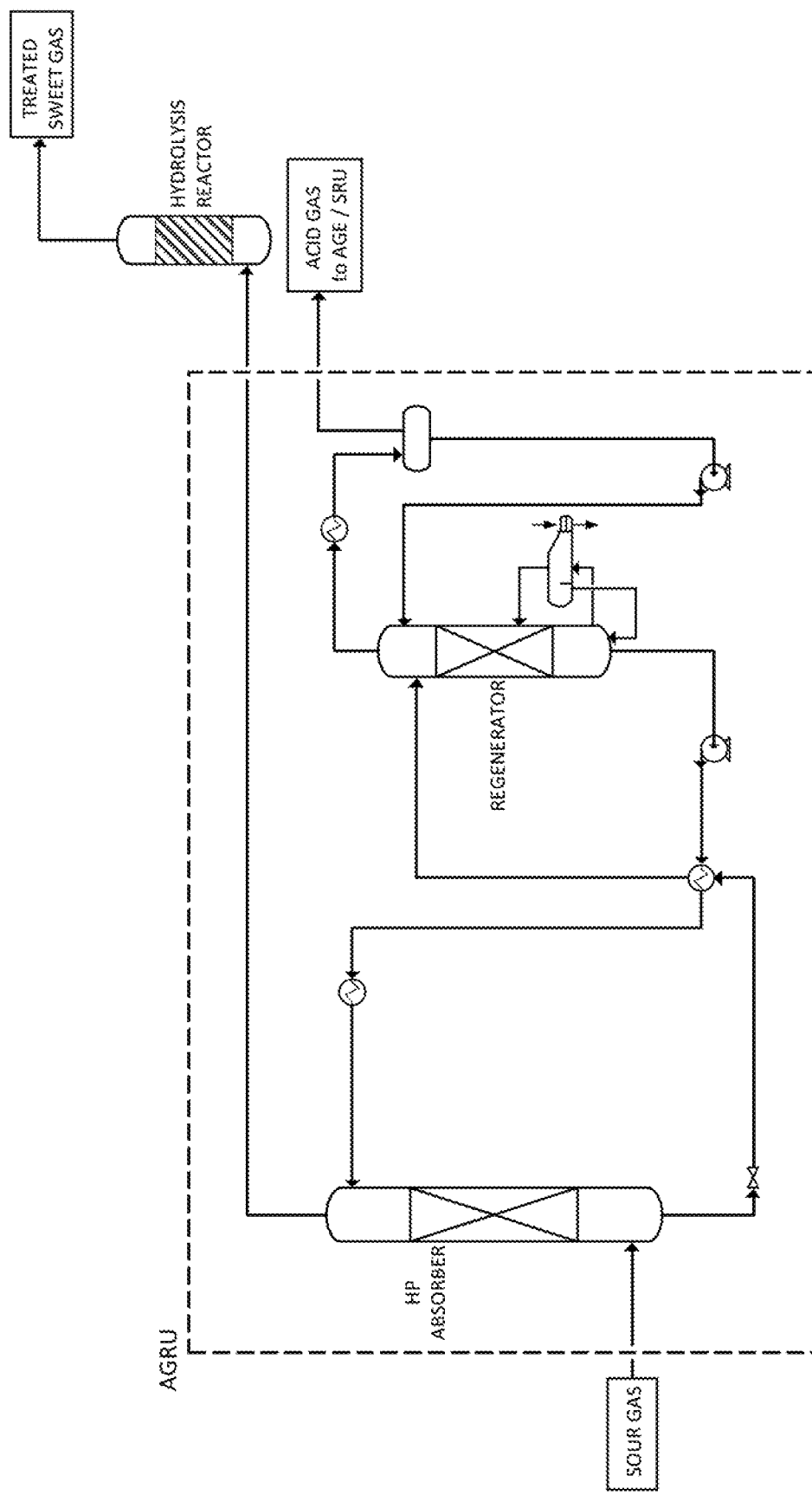
FIG. 3 is a schematic drawing of an acid gas removal unit of a sulphur recovery facility as modified in accordance with an embodiment of the invention, having a hydrolysis reactor on top of an HP absorber.

FIG. 3 is a schematic drawing of an acid gas removal unit of a sulphur recovery facility as modified in accordance with an embodiment of the invention; shown is the presence of a hydrolysis reactor on top of an HP absorber.

Figure 4:
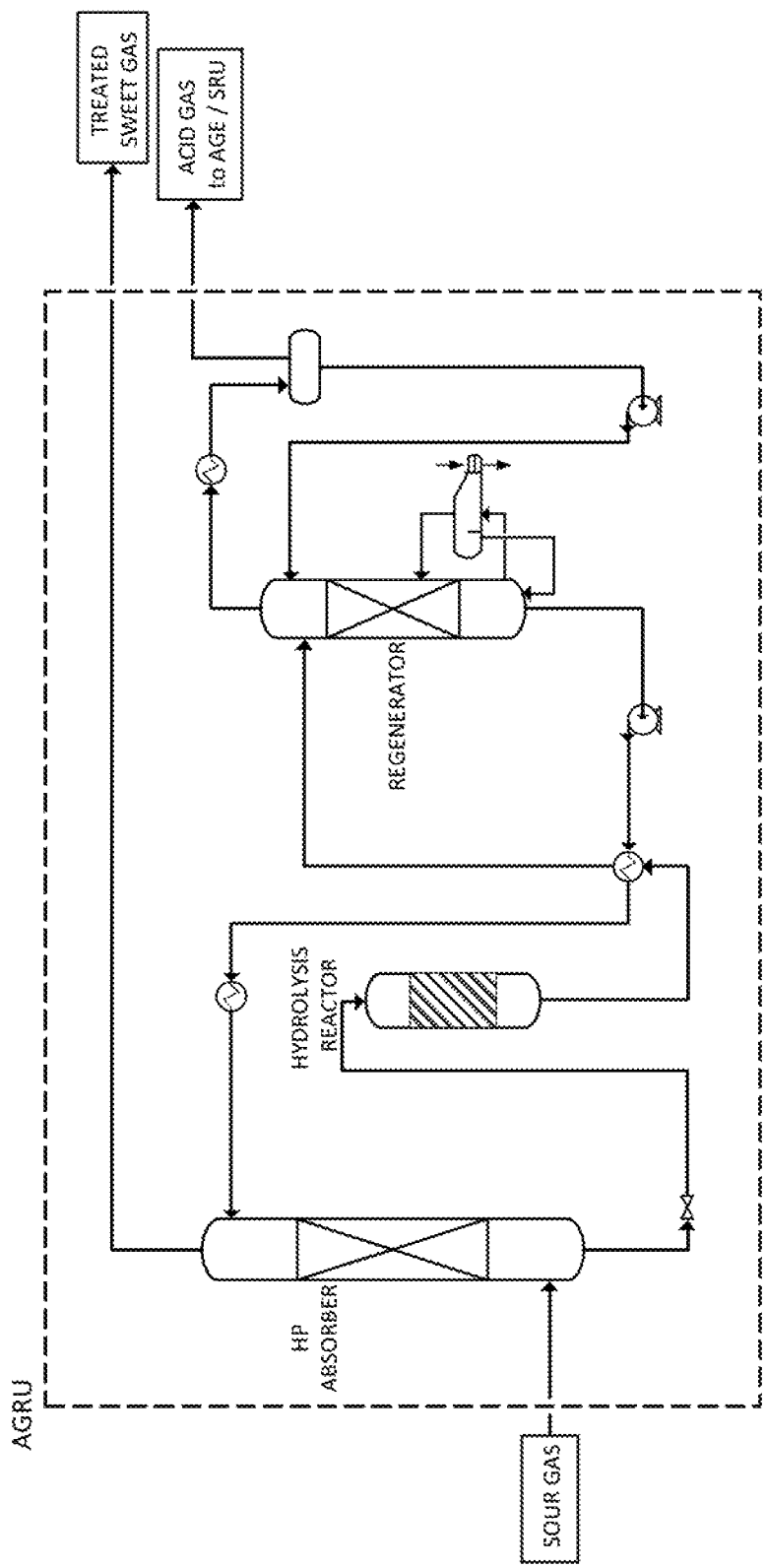
FIG. 4 is a schematic drawing of an acid gas removal unit of a sulphur recovery facility as modified in accordance with an embodiment of the invention, having a hydrolysis reactor between the bottom of an absorber and an LP regenerator.

FIG. 4 is a schematic drawing of an acid gas removal unit of a sulphur recovery facility as modified in accordance with an embodiment of the invention; shown is the presence of a hydrolysis reactor between the bottom of an absorber and an LP regenerator.

Figure 5:
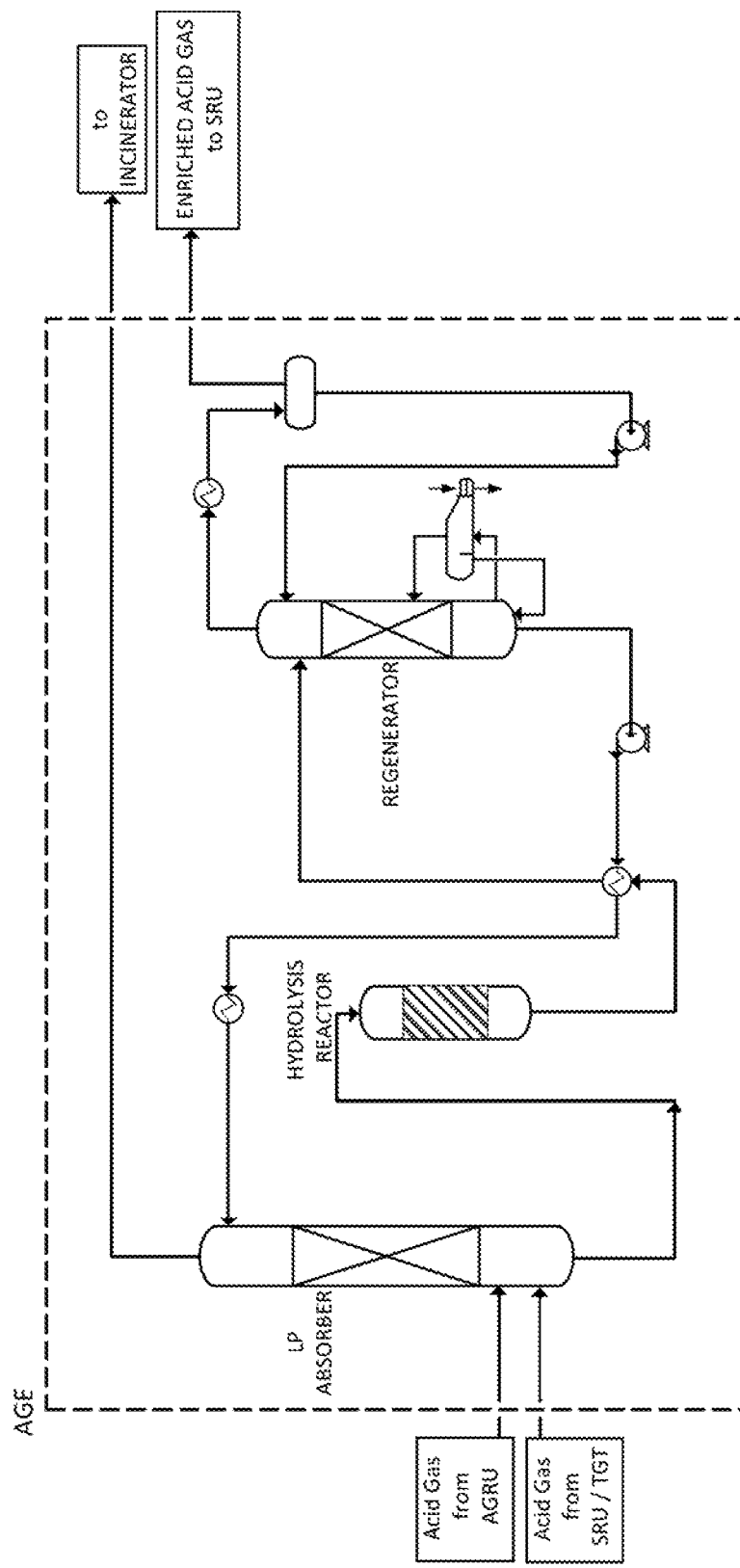
FIG. 5 is a schematic drawing of an acid gas enrichment section of a sulphur recovery facility as modified in accordance with an embodiment of the invention, having a hydrolysis reactor between the bottom of an LP absorber and an LP regenerator.

FIG. 5 is a schematic drawing of an acid gas enrichment section of a sulphur recovery facility as modified in accordance with an embodiment of the invention, having a hydrolysis reactor between the bottom of an LP absorber and an LP regenerator.

The main operating conditions preferably employed are:
Feedstock: Sour gas (C1, C2, C3, C4, C6+)
Feedstock temperature: 20° C.-80° C.
Feedstock pressure: >0.01 barg
Type of absorption liquid: MEA, DEA, MDEA, DIPA, DGA, special formulated amine solution, commercial physical solvents, any mixture of them, with or without additive addition.
Absorption liquid temperature: 20° C.–150° C.
Absorption liquid concentration of amines: 5 wt. %-95 wt %
COS and/or $CS_2$ conversion in liquid phase via hydrolysis with catalyst: >>50% depending on the type of amine (prior art typically achieves <50%)
Percentage of deposited catalyst on structured support or any contacting device: <30 wt. %
Catalyst installation: upgrading of conventional equipment (columns, 3 phase separators, heat exchangers, filters, flash vessel, tank) or in a dedicated equipment (reactor).

The invention is hereinafter illustrated with reference to the following non-limiting Example.

Example

In this example, a homogeneous catalyst is used, i.e. a metal salt in aqueous solution. Examples of salts employed are: $NH_4VO_3$ (ammonium metavanadate); $C_{10}H_{14}FeO_4$ (ferrous acetylacetonate); $(C_5H_8O_2)_3Ru$ (ruthenium(III)acetylacetonate); $(NH_4)Mo_7O_{24}*4H_2O$ (diammonium heptamolybdate tetrahydrate).

P=0.1 barg

Absorption liquid temperature=25° C.

Absorption liquid concentration, the liquid being an aqueous solution of diethanol amine (DEA) of 15 wt. %

Feedstock COS concentration: 125 ppm-1000 ppm

Vanadium concentration in the solution: 0.13 M

In the presence of the catalyst, the removal of COS through a hydrolysis reaction is one order of magnitude higher than that obtained in the absence of catalyst.

The invention claimed is:

1. A reactor system for removing carbonyl sulphide (COS) and/or carbon disulphide ($CS_2$) from a sour gas stream, wherein the reactor system comprises an absorption column, wherein the absorption column contains an absorption liquid and comprises a catalyst suitable for hydrolyzing COS and $CS_2$, wherein the catalyst is a transition metal or a salt of a transition metal, and wherein the catalyst is present in or on the absorption column.

2. The reactor system of claim 1, wherein the absorption column comprises trays, wherein the catalyst is a heterogeneous catalyst applied as a coating on the trays.

3. The reactor system of claim 1, wherein the absorption column is a packed column with a packing, wherein the catalyst is coated on the packing.

4. The reactor system of claim 1, wherein the catalyst is selected from the group consisting of vanadium, iron, molybdenum, ruthenium, manganese, chromium, zinc, nickel, and salts thereof, and combinations thereof.

5. A reactor system for removing COS and/or $CS_2$ from a sour gas stream, comprising an absorption vessel that is configured to subject the sour gas stream to contact with an absorption liquid so as to produce a liquid stream containing absorbed gas and having an outlet for said liquid stream; and a hydrolysis reactor having an inlet that is connected to said outlet for said liquid stream of said absorption vessel and that is configured to receive said liquid stream from said absorption vessel, wherein the hydrolysis reactor comprises a catalyst suitable for hydrolyzing COS and $CS_2$, and whereby the liquid stream is contacted with said catalyst in said hydrolysis reactor.

6. The reactor system of claim 5, wherein the catalyst is a transition metal or a salt of a transition metal.

7. The reactor system of claim 1, wherein the absorption liquid is an alcohol or a basic aqueous solution.

8. The reactor system of claim 5, wherein said hydrolysis reactor further comprises a contacting device and wherein the catalyst is deposited on said contacting device, wherein said contacting device is selected from the group consisting of filtering media, vane packs, corrugated plates, coalescing media, and flashing devices.

9. The reactor system of claim 5, wherein said reactor system further comprises a regenerator connected to a liquid outlet of the hydrolysis reactor and wherein the outlet of said absorption vessel is at the bottom of the absorption vessel and is connected to said inlet of said hydrolysis reactor that configured to receive liquid from said absorption vessel.

10. The reactor system of claim 1, wherein the absorption column has a top and a bottom, and has a liquid inlet for the absorption liquid at said top and a liquid outlet at said bottom, and an inlet for said sour gas stream at said bottom and an outlet for a treated gas stream at said top.

* * * * *